United States Patent
Horng

(10) Patent No.: US 8,697,884 B2
(45) Date of Patent: Apr. 15, 2014

(54) METHOD OF MANUFACTURING CYCLIC CARBONATE BY USING IONIC LIQUID POLYMER

(75) Inventor: Shiey-Shiun Horng, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 0 days.

(21) Appl. No.: 13/446,702

(22) Filed: Apr. 13, 2012

(65) Prior Publication Data

US 2013/0274485 A1    Oct. 17, 2013

(51) Int. Cl.
*C07D 233/00* (2006.01)

(52) U.S. Cl.
USPC ...................................................... 548/300.1

(58) Field of Classification Search
USPC ...................................................... 549/228
See application file for complete search history.

(56) References Cited

U.S. PATENT DOCUMENTS

| | | |
|---|---|---|
| 7,365,214 B2 | 4/2008 | Srinivas et al. |
| 7,589,227 B2 | 9/2009 | Buchold et al. |
| 2006/0094893 A1 | 5/2006 | Srinivas et al. |
| 2010/0048918 A1 | 2/2010 | Yeo et al. |

OTHER PUBLICATIONS

Xie, Y., et al. "Cycloaddition Reactions Catalyzed by an Ionic Liquid Grafted onto a Highly Cross-Linked Polymer Matrix." Angew. Chem. Int. Ed. (2007), vol. 46, pp. 7255-7258.*
Sun, J., et al. "Reusable and efficient polymer-supported task-specific ionic liquid catalyst for cycloaddition of epoxide with CO2." Catalysis Today. (2009), vol. 148, pp. 361-367.*
H. S. Kim et al., "Imidazolium zinc tetrahalide-catalyzed coupling reaction of $CO_2$ and ethylene oxide or propylene oxide" *Journal of Catalysis* 220 (2003) pp. 44-46.

* cited by examiner

*Primary Examiner* — Taofiq A Solola
*Assistant Examiner* — John S Kenyon
(74) *Attorney, Agent, or Firm* — Muncy, Geissler, Olds & Lowe, P.C.

(57) ABSTRACT

A method of manufacturing cyclic carbonate comprises a step of "preparation," by preparing an ionic liquid polymer; and a step of "cyclization," by feeding carbon dioxide and epoxide into a reactor containing the ionic liquid polymer to conduct a cyclization of the carbon dioxide and the epoxide in a batch or continuous reaction manner under the catalysis of the ionic liquid polymer, and finally to produce cyclic carbonate.

7 Claims, 8 Drawing Sheets

METHOD OF MANUFACTURING CYCLIC CARBONATE BY USING IONIC LIQUID POLYMER

BACKGROUND OF THE INVENTION

1. Field of the Invention

The present invention relates to a method of manufacturing cyclic carbonate and, more particularly, to a method of manufacturing cyclic carbonate by conducting the cyclization of carbon dioxide and epoxide under the performance of an ionic liquid polymer.

2. Description of the Related Art

Generally, cyclic carbonate is obtained via a phosgenation method, by mixing carbon monoxide and chlorine to obtain phosgene (also known as $COCl_2$), and triggering off a reaction of the phosgene and phenol or ethanol. For example, bisphenol and phosgene are prepared and carried out a synthesis reaction of cyclic carbonate under the performance of alkaline solution and dichloromethane, wherein the co-product of the synthesis reaction of cyclic carbonate is hydrochloric acid. However, due to the toxicity of phosgene and dichloromethane, the above synthesis method of cyclic carbonate is highly risky to human and natural environment, and which may imply potential dangers or pollutions.

Currently, carbon dioxide has replaced the phosgene and becomes a main material for synthesis of cyclic carbonate, by cyclizating carbon dioxide and epoxide to produce cyclic carbonate. Generally, the carbon dioxide used in the synthesis of cyclic carbonate is mainly recycled from the co-products of various industries, for example, fermentation industry, petrochemical industry and metalworking industry, and therefore, the synthesis of cyclic carbonate can be achieved in a not only eco-friendly, but economic and convenient pathway.

As disclosed in a journal article reported by Parshall in 1972 and Kim et al. in 2003, a conventional synthesis method of cyclic carbonate is provided by recycling carbon dioxide from various industries, conducting a cyclization of the recycled carbon dioxide and epoxide under the performance of an ionic solution, and finally generating cyclic carbonate. The said conventional synthesis method for cyclic carbonate comprises a step of "catalytic preparation," by preparing an ionic solution of 1-butyl-3-methylimidazolium bromide [also known as (Bmim)Br], which is in the form of sticky liquid; a step of "cyclization," by conducting a cyclization of carbon dioxide and propylene oxide in a stainless reactor, under the catalysis of zinc oxide and the (Bmim)Br, to obtain a mixed solution of propylene carbonate; and a step of "isolation," by isolating liquid propylene carbonate from the mixed solution of propylene carbonate via a distillation method.

Although the said conventional synthesis method of cyclic carbonate improves the disadvantages of the phosgenation method, the catalysis of the ionic solution of the said conventional synthesis still has the following weaknesses. First of all, the said conventional synthesis of cyclic carbonates is a time-consuming and low-efficient process because of the homogeneous catalysis between the ionic solution and the mixed solution of propylene carbonate, and therefore, an additional step of "isolation" is needed after the step of "cyclization" for the sake of isolating liquid propylene carbonate from the mixed solution of propylene carbonate via a distillation method. In this way, the cost and manufacture time of cyclic carbonate will be increased. Second, the distillation method in the step of "isolation" is generally performed by heating the ionic solution and then separating the cyclic carbonate from the ionic solution by their difference of boiling point, so that the quality of the ionic solution may be degraded after heating.

Thus, regarding the disadvantages of the conventional synthesis method of cyclic carbonate, there is a need to provide a new method of manufacturing cyclic carbonate so as to synthesize cyclic carbonate in a more convenient and effective process.

SUMMARY OF THE INVENTION

The primary objective of the present invention is to provide a method of manufacturing cyclic carbonate, by directly obtaining cyclic carbonate via a heterogeneous catalysis so that the wasteful in use of catalyst can be avoided, with the synthesis of cyclic carbonate in a more convenient and economic process.

The secondary objective of the present invention is to provide a method of manufacturing cyclic carbonate, which can directly recycle catalyst from a heterogeneous catalysis and avoid the degradation of the recycled catalyst, so as to be dramatically frugal in catalyst use.

Another objective of the present invention is to provide a method of manufacturing cyclic carbonate, by directly recycling catalyst from a heterogeneous catalysis, so that a time-consuming and costly process can be avoided.

A method of manufacturing cyclic carbonate comprises a step of "preparation," by preparing and placing an ionic liquid polymer in a reactor; and a step of "cyclization," by feeding carbon dioxide to mix with epoxide molecules, and then a cyclization of the epoxide with the carbon dioxide can be taken place in a batch or continuous reaction manner under the catalysis of the ionic liquid polymer, and finally to produce cyclic carbonate. The present invention will become clearer in light of the following detailed description of illustrative embodiments of this invention described in connection with the drawings.

BRIEF DESCRIPTION OF THE DRAWINGS

The illustrative embodiments may best be described by reference to the accompanying drawings where.

All figures are drawn for ease of explanation of the basic teachings of the present invention only; the extensions of the figures with respect to number, position, relationship, and dimensions of the parts to form the preferred embodiments will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

Figure 1:
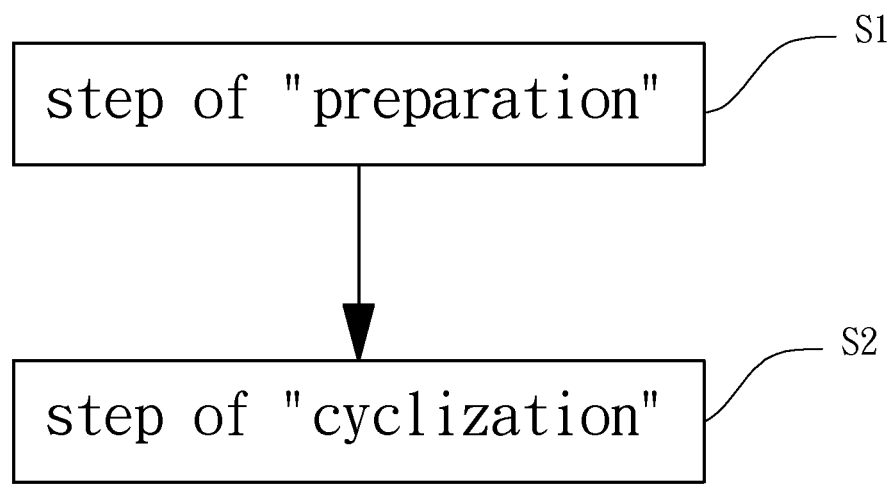
FIG. 1 is a diagram illustrating a first embodiment of the method of manufacturing cyclic carbonate in the present invention.

Referring to FIG. 1, in accordance with a first preferable embodiment of the present invention, there is a method of manufacturing cyclic carbonate comprises a step of "preparation S1," and a step of "cyclization S2."

In the step of "preparation S1," an ionic liquid polymer is prepared and placed in a reactor. More precisely, the ionic liquid polymer is one of solid materials, and is capable of being catalytic in any synthesis reaction of cyclic carbonate, for example in batch reaction or in continuous reaction. As an example, the ionic liquid polymer of the preferable embodiment is poly(1-vinylimidazolium bromide), which is placed in the reactor for catalyzing the following step of "cyclization S2."

In the step of "cyclization S2," carbon dioxide is fed to mix with epoxide molecules and a cyclization is carried out in a batch or continuous reaction manner, in order to generate cyclic carbonate under the catalysis of the ionic liquid polymer. Specifically, the epoxide placed into the reactor is mixed up with the ionic liquid polymer, wherein the epoxide can be ethylene oxide or propylene oxide and is capable of being used in a batch reaction. In the present embodiment, a preferable ratio of the ionic liquid polymer and epoxide is 0.0001 to 20.0. Next, the carbon dioxide is aerated into the reactor via a high-pressured gas cylinder, with the pressure difference between the high-pressured gas cylinder and the reactor causing the flowing of the carbon dioxide from the high-pressured gas cylinder to the reactor. With such arrangement, the cyclization of the carbon dioxide and epoxide can be taken place under the catalysis of the ionic liquid polymer, to obtain the cyclic carbonate of the present invention. Moreover, the carbon dioxide can be in the form of gas or supercritical fluid. As an example, 0.5 to 5.0 mmole of poly(1-vinylimidazolium bromide) and 10 ml of propylene oxide are mixed in the reactor to obtain a mix of poly(1-vinylimidazolium bromide) and propylene oxide, followed by aerating carbon dioxide into the reactor from a high-pressured gas cylinder set pressure at 10 atm first. Next, with reference to REACTION 1, the temperature of the buffer tank is adjusted to 50° C. to 100° C. for 0.5 hour, and then shifted to 80° C. to 250° C., also with the carbon dioxide increasing till 20 atm for 0.5 to 21 hours, in order to conduct the cyclization of carbon dioxide and epoxide under the catalysis of the ionic liquid polymer. With such arrangement, liquid propylene carbonate can be obtained in the present invention. Wherein, due to the solid phase of the poly(1-vinylimidazolium bromide), a heterogeneous catalysis is performed between the poly(1-vinylimidazolium bromide) and propylene oxide in the present invention, so as to be easy to recycle the poly(1-vinylimidazolium bromide) after reaction.

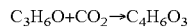
$$C_3H_6O + CO_2 \rightarrow C_4H_6O_3 \qquad \text{REACTION 1}$$

Figure 2:
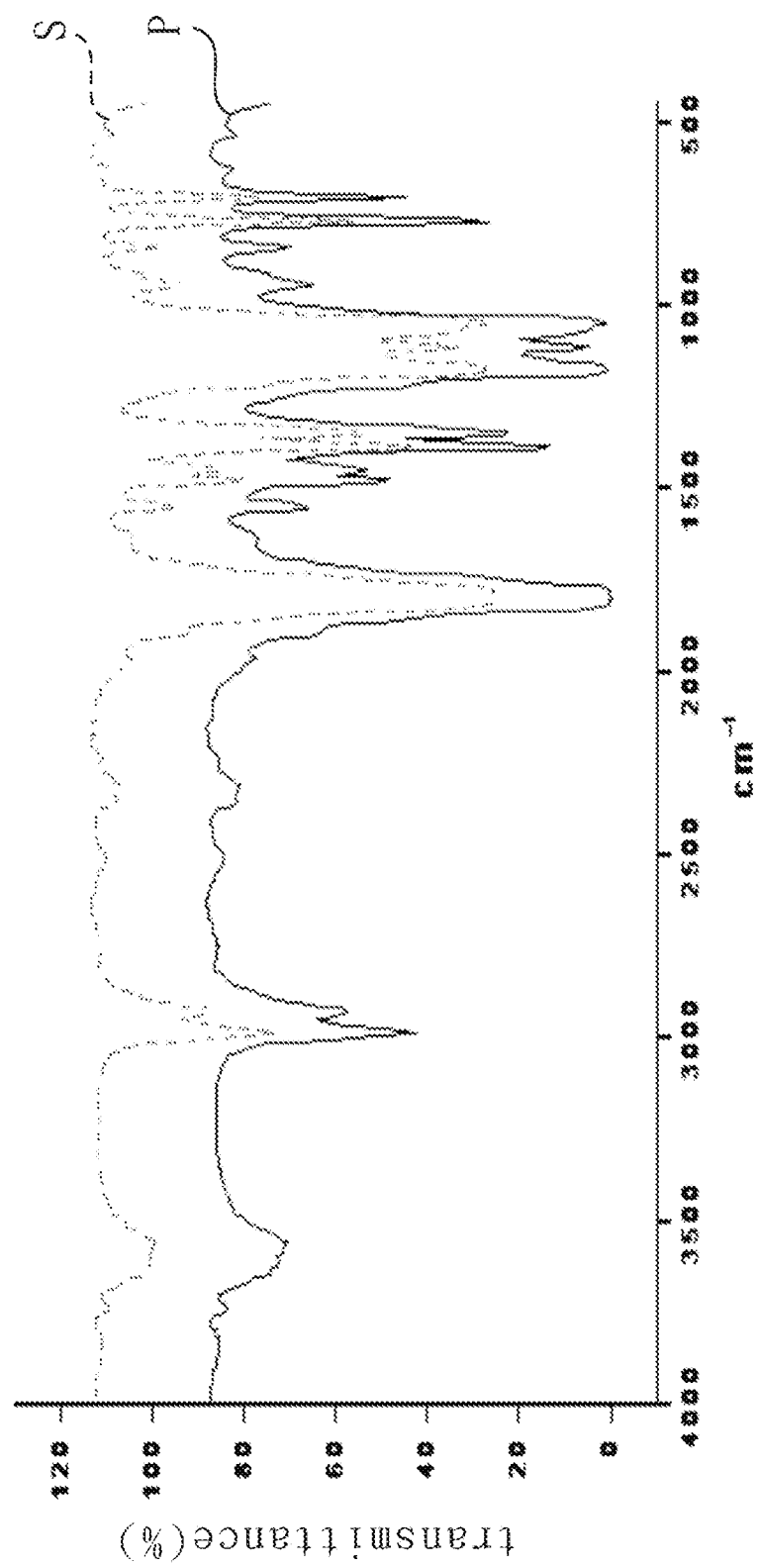
FIG. 2 is a FT-IR datum of propylene carbonate.

Referring to FIG. 2, a standard of propylene carbonate (S) and the propylene carbonate (P) obtained from the present invention are both analyzed by a Fourier Transform Infrared Spectroscopy (also known as FT-IR). In FIG. 2, the curve of the propylene carbonate (P) is similar to that of the standard of propylene carbonate (S), with both of them showing vibrating peaks of C=O and C—O—C at 1783 cm$^{-1}$ and at 1310 to 1000 cm$^{-1}$ respectively. It is confirmed that the only product of the present invention is propylene carbonate, with high purity.

In summary, the cyclization of carbon dioxide and epoxide of the present invention can produce high purity of propylene carbonate under the catalysis of poly(1-vinylimidazolium bromide). Furthermore, according to the heterogeneous catalysis between the ionic liquid polymer, carbon dioxide and liquid propylene oxide, the ionic liquid polymer can be directly reused after the cyclization of carbon dioxide and epoxide, so that the quality of the ionic liquid polymer can be successfully maintained, instead of being degraded by high temperature. With such advantages of the present invention, the synthesis of cyclic carbonate can be achieved in a time-saving process, which is significantly fugal in catalyst use.

Figure 3:
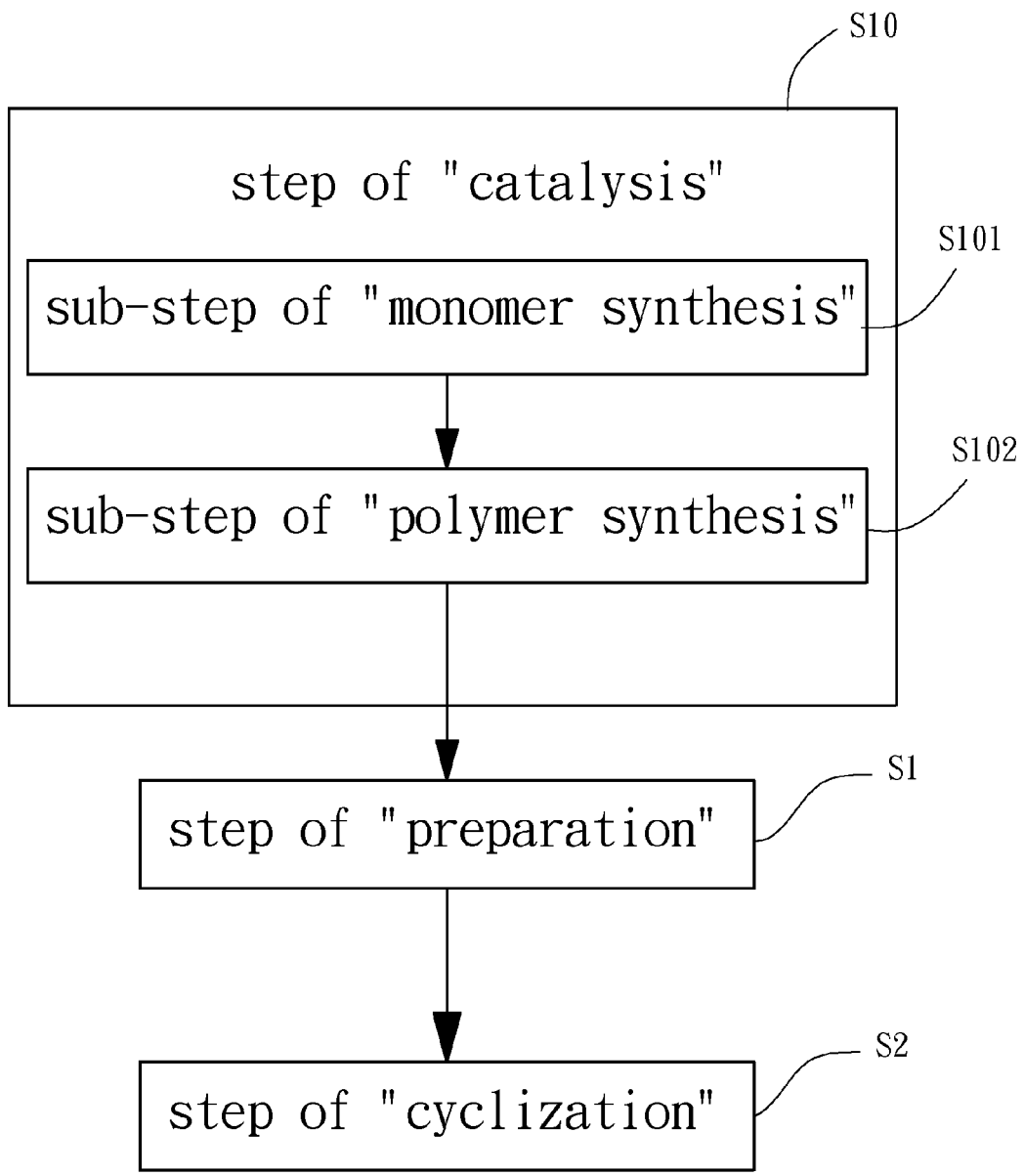
FIG. 3 is a diagram illustrating a second embodiment of the method of manufacturing cyclic carbonate in the present invention.

In FIG. 3, there is a second preferable embodiment of the method of manufacturing cyclic carbonate in the present invention. Comparing with the first embodiment of the present invention, the said method further comprises a step of "catalyst preparation S10" before the step of "preparation S1" by synthesizing the ionic liquid polymer.

In the step of "catalyst S10," an addition polymerization of imidazolium liquid monomer is carried out under the performance of a polymerization initiator, in order to obtain the ionic liquid polymer, wherein the ionic liquid polymer is solid and is capable of being used as a catalyst in a synthesis reaction of cyclic carbonate. Precisely, the ionic liquid polymer is generated by polymerizing an ionic liquid monomer, such as imidazolium liquid monomer under the performance of the polymerization initiator, wherein the ionic liquid monomer is consisted of anion and cation, and the polymerization initiator can be 2,2'-azobisisobutyronitrile. Preferably, the ionic liquid monomer is selected from one of alkenylimidazolium ionic liquid, for example 1-vinylimidazole.

Additionally, with reference to FIG. 3, the addition polymerization of the imidazolium liquid monomer further comprises two sub-steps including a sub-step of "monomer synthesis S101," and a sub-step of "polymer synthesis S102." In the sub-step of "monomer synthesis S101," an alkyl reaction of the alkenylimidazolium ionic liquid and a haloalkanes, such as 1-bromoethanol and 2-bromoethanol, is performed to produce an alkenylimidazolium halide, being the ionic liquid monomer of the present invention. Next, in the sub-step of "polymer synthesis S102," an addition polymerization of the alkenylimidazolium halide is conducted under the performance of the polymerization initiator to obtain poly(alkenylimidazolium haloid) as the ionic liquid polymer of the present embodiment. Furthermore, the poly(alkenylimidazolium haloid) can be one of poly[1-(2-hydroxyl-ethyl)-3-vinylimidazolium bromide], poly(1-vinyl-3-alkyl imidazolium bromide) and poly [1-vinly-3-(ω-hydroxyl-alkyl) imidazolium bromide].

Figure 4:
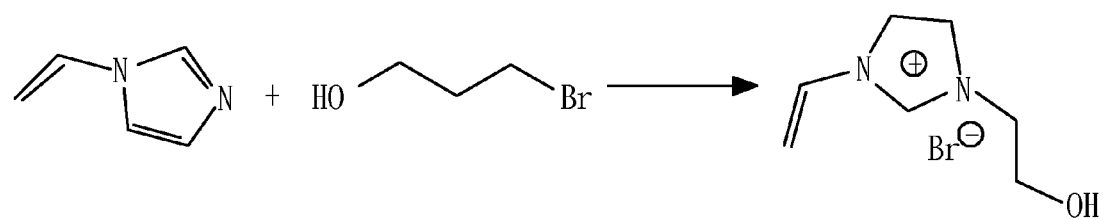
FIG. 4 is a chemical reaction of the step of "monomer synthesis" in the present invention.

With reference to FIG. 4, 0.14 mmloe of 1-vinylimidazole, being the imidazolium liquid monomer, and 50 ml of toluene are mixed to obtain a mixture, followed by sequentially dropping 0.16 mmole of 2-bromoethanol into the mixture to trigger off an alkylation of the 1-vinylimidazole and the 2-bromoethanol. Then, a solution with two phase of layering is obtained after three days of reaction, wherein the lower layer of the solution is further isolated and repeatedly washed by toluene and ether, followed by being condensed and dried in vacuo for 1 hour, to obtain 1-(2-hydroxyl-ethyl)-3-vinylimidazolium bromide (also known as HEVIMB).

Figure 5:
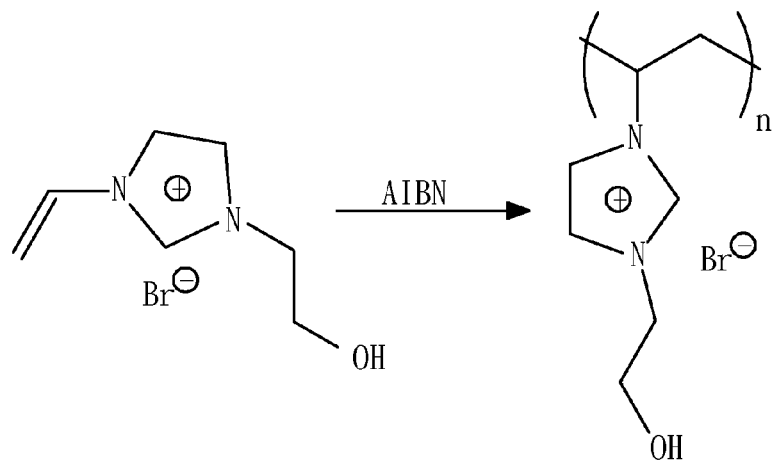
FIG. 5 is a chemical reaction of the step of "polymer synthesis" in the present invention.

Sequentially, with reference to FIG. 5, an addition polymerization of the 1-(2-hydroxyl-ethyl)-3-vinylimidazolium bromide is conducted by dissolving and mixing 5 g of 1-(2- hydroxyl-ethyl)-3-vinylimidazolium bromide in 15 ml ethanol to obtain a solution; adding 5 wt % of 2,2-azobisisobutyronitrile into the solution, followed by heating at 70° C. for 1 day; and finally obtaining a yellow turbid solution after reaction. The yellow turbid solution is further treated by acetone to collect the precipitates, dried for 30 minutes in vacuo and obtain poly(1-2-hydroxyl-ethyl)-3-vinylimidazolium bromide, also known as PHEVIMB. The poly (1-2-hydroxyl-ethyl)-3-vinylimidazolium bromide can be used as a catalyst in the method of manufacturing cyclic carbonate in the present invention.

Figure 6:
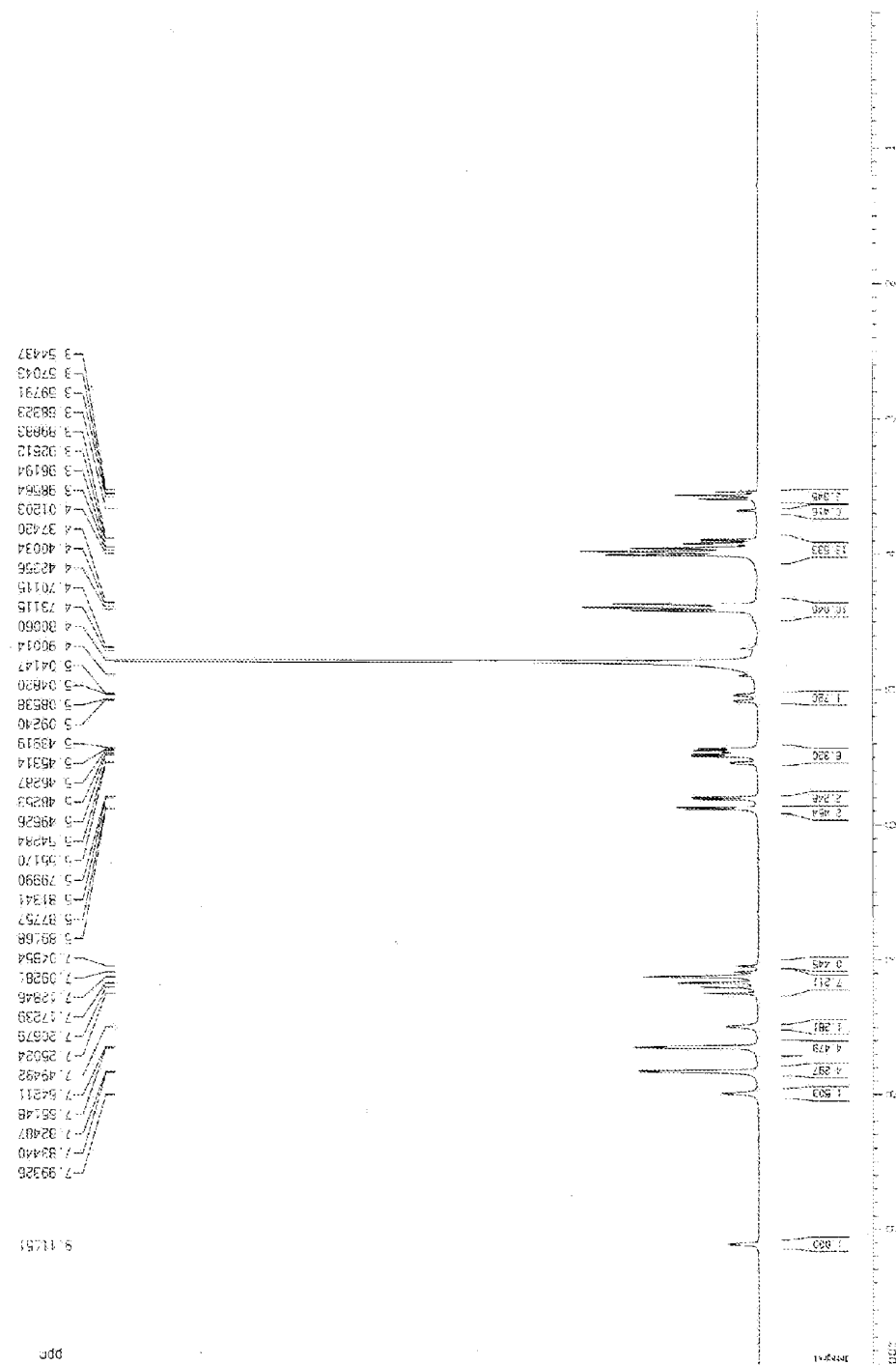
FIG. 6 is a $^1$H-NMR datum of 1-(2-hydroxyl-ethyl)-3-vinylimidazolium bromide in the present invention.
Figure 7:
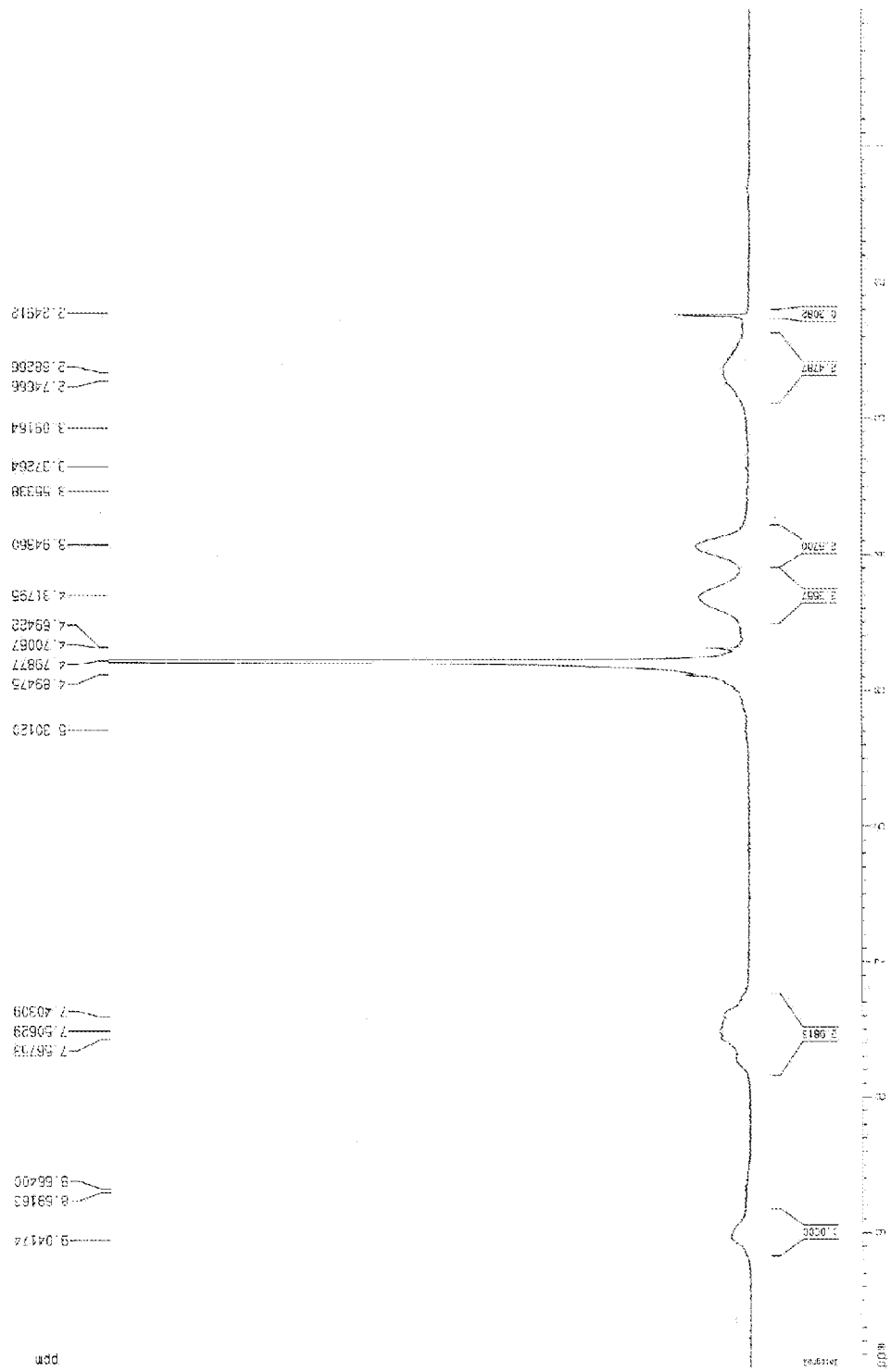
FIG. 7 is a $^1$H-NMR diagram of poly(1-2-hydroxyl-ethyl)-3-vinylimidazolium bromide of the present invention.

In FIGS. 6 and 7, the 1-(2-hydroxyl-ethyl)-3-vinylimidazolium bromide and the poly(1-2-hydroxyl-ethyl)-3-vinylimidazolium bromide are analyzed by $^1$H-NMR, wherein the 1-(2-hydroxyl-ethyl)-3-vinylimidazolium bromide has absorbed peaks of hydrogen at $\delta$=7.1, 5.8 and 5.4, but the poly (1-2-hydroxyl-ethyl)-3-vinylimidazolium bromide has no signal at $\delta$=5.4 to 7.1. It is suggested that the bond of the ethylene monomer and hydrogen in the 1-(2-hydroxyl-ethyl)-3-vinylimidazolium bromide are broken during the addition polymerization of 1-(2-hydroxyl-ethyl)-3-vinylimidazolium, and therefore, the ionic liquid polymer of the present invention is successfully generated via the addition polymerization of the ionic liquid monomer. Moreover, the ionic liquid polymer is sufficient to be used in the method of manufacturing cyclic carbonate of the present invention, as a catalyst thereof.

In the following paragraphs, the catalytic effects of the ionic liquid polymer on the cyclization of carbon dioxide and epoxide are demonstrated, by monitoring and recording the yield of the propylene carbonate under various reaction conditions, such as different reaction time, temperature, and concentration of the ionic liquid polymer.

Figure 8:
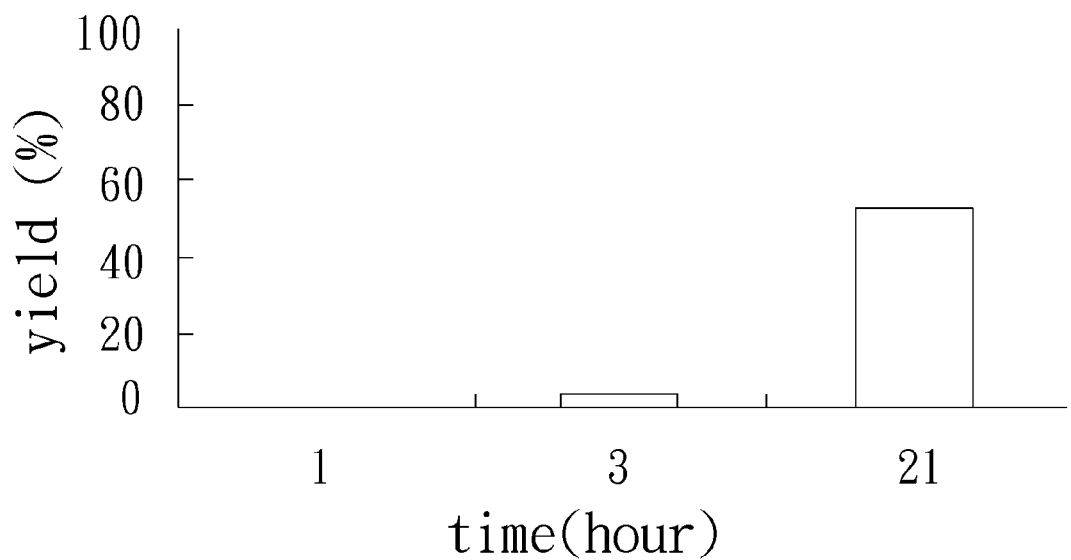
FIG. 8 is a bar chart illustrating the yield of propylene carbonate with respect to reaction time.
Figure 9:
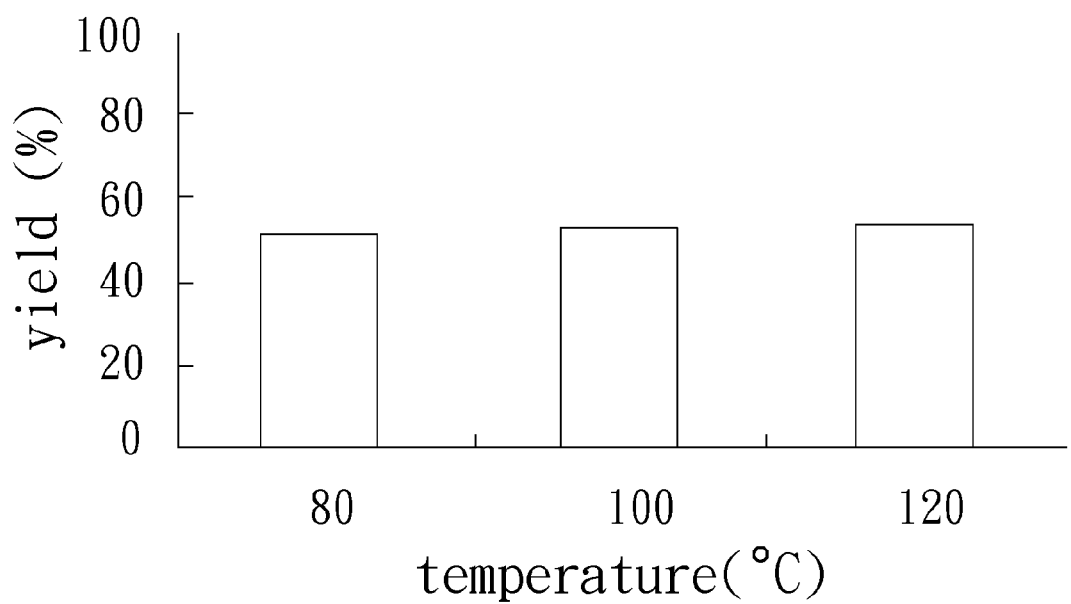
FIG. 9 is a bar chart illustrating the yield of propylene carbonate with respect to reaction temperature.

According to FIG. 8 and 9, 20 atm of carbon dioxide and 10 ml of propylene oxide are prepared and carried out a cyclization reaction under the catalysis of 1.39 mmole of poly (1-2-hydroxyl-ethyl)-3-vinylimidazolium bromide, wherein the conditions of the cyclization of propylene oxide with carbon dioxide are adjusted to 100° C. for 1, 3, and 21 hours, and 80, 100, and 120° C. for 21 hours respectively, and the yield of propylene carbonate under various conditions is gradually improved.

In FIGS. 8 and 9, it is noted that the yield of propylene carbonate increases with the increase of reaction time, but has no difference under various temperatures. Accordingly, a preferable time of the cyclization of the present invention is 21 hours, and a preferable temperature for the cyclization of the present invention is at 100° C.

Figure 10:
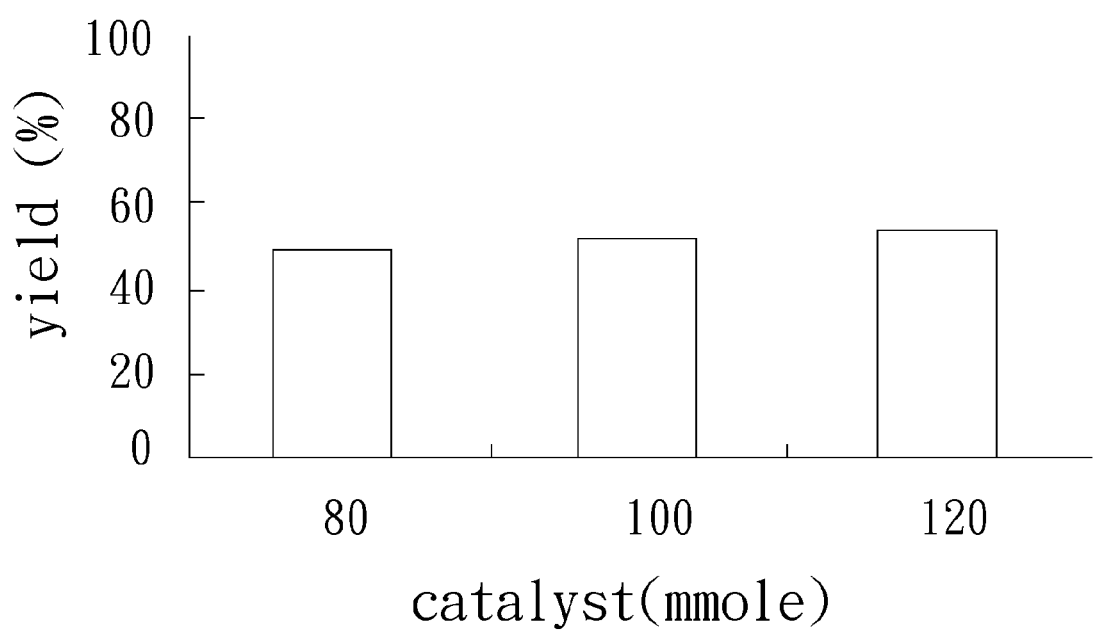
FIG. 10 is a bar chart illustrating the yield of propylene carbonate with respect to the amount of catalyst.

Next, in accordance with FIG. 10, 20 atm of carbon dioxide and 10 ml of propylene oxide are prepared and carried out a cyclization under the catalysis of poly (1-2-hydroxyl-ethyl)-3-vinylimidazolium bromide at 100° C. for 21 hours, wherein the concentration of the poly (1-2-hydroxyl-ethyl)-3-vinylimidazolium bromide selected from a group of 1.39, 1.86, and 2.32 mmol to study the effects of concentration of the catalyst on the cyclization of carbon dioxide and epoxide.

In FIG. 10, it is shown that the yield of the propylene carbonate slightly increases with the increase of the concentrate of the catalyst. Also, it is believed that the ionic liquid polymer of the present invention is sufficient to be used in the synthesis of cyclic carbonate and catalyzing the cyclization of the carbon dioxide and epoxide, so as to obtain high quality of propylene carbonate in the present invention.

Through the present invention, a method of manufacturing cyclic carbonate is provided by directly producing cyclic carbonate via a heterogeneous catalyst under the catalysis of an ionic liquid polymer. With such arrangement, the synthesis of cyclic carbonate can be achieved in a convenient and economical process, and also the ionic liquid polymer of the present invention can be directly reused in a continuous manner, and therefore, the repetitive catalyst preparation during manufacturing process could be avoided so as to be dramatically frugal in catalyst use in the present invention.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method of manufacturing cyclic carbonate comprising:
    a preparation step of preparing and placing an ionic liquid polymer in a buffer tank, wherein, the ionic liquid polymer is a poly(alkenylimidazolium haloid) being selected from poly[1(2hydroxyl-ethyl)-3-vinylimidazolium bromide], poly(1-vinyl-3-alkyl imidazolium bromide) or poly[1-vinyl-3-(ω-hydroxyl-alkyl) imidazolium bromide]; and
    a cyclization step of catalyzing a cyclization reaction of a carbon dioxide with an epoxide in a batch or continuous reaction manner under the catalysis of the ionic liquid polymer, and finally to produce cyclic carbonate.

2. The method of manufacturing cyclic carbonate as claimed in claim 1, wherein a catalysis step is performed before the preparation step and, the catalysis step conducting an addition polymerization of an imidazolium ionic liquid monomer under the performance of a polymerization initiator to obtain the ionic liquid polymer.

3. The method of manufacturing cyclic carbonate as claimed in claim 2, wherein, in the catalysis step, the polymerization initiator is 2,2'-2,2'-azobisisobutyronitrile.

4. The method of manufacturing cyclic carbonate as claimed in claim 2, wherein, in the catalysis step, the imidazolium ionic liquid monomer is alkenylimidazole.

5. The method of manufacturing cyclic carbonate as claimed in claim 4, wherein the catalysis step comprises a sub-step of monomer synthesis conducting an alkylation between the alkenylimidazole and a haloalkanes to obtain an alkenylimidazolium halide and another sub-step of polymer synthesis conducting the addition polymerization of the alkenylimidazolium halide under the performance of the polymerization initiator to obtain the poly(alkenylimidazolium haloid) as the ionic liquid polymer.

6. The method of manufacturing cyclic carbonate as claimed in claim 1, wherein, in the cyclization step, the temperature of the cyclization of the carbon dioxide is at 80° C. to 250° C.

7. The method of manufacturing cyclic carbonate as claimed in claim 1, wherein, in the cyclization step, the reaction time of the cyclization of the carbon dioxide and the epoxide is 0.5 to 21 hours.

* * * * *